United States Patent
Aita et al.

(10) Patent No.: US 6,869,701 B1
(45) Date of Patent: Mar. 22, 2005

(54) SELF-REPAIRING CERAMIC COATINGS

(75) Inventors: Carolyn R. Aita, Shorewood, WI (US); Vladislav V. Yakovlev, Milwaukee, WI (US); Mary M. Cayton, Germantown, WI (US); Mahmood Mirhoseini, Germantown, WI (US); Michael Aita, Shorewood, WI (US)

(73) Assignee: Carolyn Aita, Shorewood, WI (US)

( * ) Notice: Subject to any disclaimer, the term of this patent is extended or adjusted under 35 U.S.C. 154(b) by 0 days.

(21) Appl. No.: 09/375,169

(22) Filed: Aug. 16, 1999

(51) Int. Cl.[7] .............................. B32B 9/04; A61L 27/02
(52) U.S. Cl. ...................... 428/698; 428/469; 428/699; 428/701; 428/702; 428/704; 428/336; 623/1.46; 623/13.18
(58) Field of Search ................................. 428/469, 701, 428/702, 704, 698, 699, 636; 623/2, 11–23, 66, 13.18, 1.44, 1.46; 148/212, 238, 537

(56) References Cited

U.S. PATENT DOCUMENTS

| | | | |
|---|---|---|---|
| 4,326,305 A | * | 4/1982 | Davidas |
| 4,847,163 A | * | 7/1989 | Shimamune et al. |
| 5,123,924 A | * | 6/1992 | Sioshansi et al. |
| 5,246,787 A | * | 9/1993 | Schulz et al. |
| 5,258,022 A | * | 11/1993 | Davidson |
| 5,372,660 A | * | 12/1994 | Davidson et al. |
| 5,443,663 A | * | 8/1995 | Meletis |
| 5,472,795 A | | 12/1995 | Atita |
| 5,496,359 A | | 3/1996 | Davidson |
| 5,649,951 A | * | 7/1997 | Davidson |
| 5,674,293 A | * | 10/1997 | Armini et al. |
| 5,676,632 A | | 10/1997 | Davidson |
| 5,685,306 A | | 11/1997 | Davidson |
| 5,690,670 A | * | 11/1997 | Davidson |
| 5,728,465 A | * | 3/1998 | Dorfman et al. |
| 5,782,910 A | * | 7/1998 | Davidson |
| 5,849,206 A | | 12/1998 | Amon et al. |
| 5,855,950 A | * | 1/1999 | Bunker |
| 5,868,796 A | * | 2/1999 | Buechel et al. |
| 5,980,974 A | * | 11/1999 | Armini et al. |
| 6,008,432 A | * | 12/1999 | Taylor |

OTHER PUBLICATIONS

Piattelli et al, Histological evaluation of bone reactions to aluminum oxide dental implants in man: a case report, Biomaterials, see entire doument.*
Meinert et al, Corrosion studies of stainless steel 316L, modified by ion beam techniques, under simulated physiological conditions, Surface Coatings and Technology.*
Kurzweg et al, Development of plasma–sprayed bioceramic coatings with bond coats based on titania and zirconia, Biomaterials.*
H.E. Kambic, 'Changing strategies for biomaterials and biotechnology', in *Biomaterials' Mechanical Properties, ASTM STP 1173* (edited by H.E. Kambic and A.T. Yokobori, Jr., American Society for Testing Materials, Philadelphia, PA, 1994) pp. 293–301.

(List continued on next page.)

*Primary Examiner*—Jennifer McNeil
(74) *Attorney, Agent, or Firm*—Edward J. Lynch; Duane Morris LLP

(57) ABSTRACT

A protective coating for a substrate is disclosed having an outer component or module formed of a swellable material and an inner module formed of a plurality of layer or bilayers formed of ceramic material. The coating comprising a plurality of modules comprising a first module comprising a number (m) of bilayers comprising zirconia and alumina wherein (m) is a number greater than 1. The coating further comprises a second module disposed on the first module comprising a number (n) of bilayers comprising zirconia and titania wherein (n) is a number greater than 1. The coating further comprises a third module disposed on the second module comprising a third-module compound capable of forming a hydrate or hydroxide compound upon contact with an oxygen containing environment.

23 Claims, 1 Drawing Sheet

As-Grown Nanolaminate

OTHER PUBLICATIONS

O.F. Bertrand, R. Mongrain, J. Rodes, J.C. Tardif, L. Bilodeau, G. Cote, and M. Bourassa, 'Biocompatibility aspects of new stent technology', *Journal of the Americna College of Cardiology* 32, 562–571 (1998).

B. Kasemo and J. Lausmaa, 'Surface properties and process of the biomaterial–tissue interface', *Materials Science and Engineering* CI, 115–119 (1994).

S.H. Teoh, S.C. Lim, E.T. Yoon, and K.S. Goh, 'A new method for in–vitro wear assessment of materials used in mechanical heart valves', in *Biomaterials' Mechanical Properties, ASTM STP 1173* (Edited by H.E. Kambic and A.T. Yakabori, Jr., American Society for Testing and Materials, Philadelphia, PA 1994) pp. 43–52.

R. Hauert, U. Müller, G. Francz, F. Birchler, A. Schroeder, J. Mayer, and E. Wintermantel, 'Surface analysis and Bioreactions of F and Si containnig a–C:H', *Thin Solid Films* 308–309, 191–194 (1997).

M. Shirkhanzadeh, 'Nanopourous alkoxy–derive titanium oxide coating: a reactive overlayer for functionalizing titanium surface', *Journal of Materials Science: Materials in Medicine* 9, 355–362 (1998).

M. Amon, A. Bolz, and M. Schaldach, 'Improvement of stenting therapy with a silicon carbide coated tantalum stent', *Journal of Materials Science: Materials in Medicine* 7, 273–278 (1996).

L.D. Piveteau, M.J. Girona, L. Schlapbach, P. Barboux, J.P. Bailot, and B. Gasser, 'Thin films of calcium phosphate and titanium dioxide by a sol–gel route: a new method for coating medical implants', *Journal of Materials Science: Materials in Medicine* 10, 161–167 (1999).

N. Maalej, R. Albrecht, and J. Loscalzo, 'The potent platelet inhibitory effect of S–nitrosated albumin coating of artificial surfaces', *Journal of the American College of Cardiology,* 33, 1408–1414 (1999).

A. Krajewski, A. Ravaglioli, and M. Mazzocchi, 'Coating of $ZrO_2$ supports with a biological glass', *Journal of Materials Science: Materials in Medicine* 9, 309–316 (1998).

Y.H. Yun, V.T. Turitto, K.P. Diagle, P. Kovacs, J.A. Davidson, and S.M. Slack, 'Initial hemocompatibility studies of titanium and zirconium alloys: Prekallikrein activation, fibrinogen absorption, and their correlation with surface electrochemical properties', *Journal of Biomedical Materials Research* 32, 77–85 (1996).

H. Gleiter, 'Materials with ultrafine microstructures: retrospectives and perspectives,' *Nanostructured Materials* 1, 1–19 (1992).

D.F. Green, R.H.J. Hannink, and M.V. Swain, 'Transformation Toughening of Ceramics', (CRC Press, Inc., Boca Raton, FL 1989) pp. 1–15.

G. Skandan, C.M. Foster, H. Frase, M.N. Ali, J.C. Parker, and H. Hahn, 'Phase characterization and stabilization due to grain size effects of nanostructured $Y_2O_3$', *Nanostructured Materials,* 1, 313–322 (1992).

G.S. Was and T. Foecke, 'Deformation and Fracture in microlaminates', *Thin Solid Films,* 286, 1–31 (1996).

R. Lappalainen and R. Raj, 'Nanograin superplasticity', in *Microcomposites and Nanophase Materials* (edited by D.C. Van Aken, G.S. Was and A.K. Ghosh, TMS, Warrendale, PA, 1991) pp. 41–51.

H. Hahn, 'Microstructure and properties of nanostructured oxides', Nanostructured Materials 2, 251–265 (1993).

H. Hahn and R.S. Averback, 'High temperature mechanical properties of nanostructured ceramics', *Nanostructured Materials* 1, 95–100 (1992).

F.A. Modine, D. Lubben, and J.B. Bates, 'Electrical conduction in $CaF_2$ and $CaF_2Al_2O_3$ nanocomposite films on $Al_2O_3$ substrates', *Journal of Applied Physics* 74, 2658–2664 (1993).

A.H.M. Zahirul, Y. Alam, Y. Takashima, K. Sasaki, and T. Hata, 'Properties of indium tin oxide films with indium tin modulation layers prepared by nano–scale controlled reactive magnetron sputtering', *Thin Solid Films* 279, 131–134 (1996).

T. Hirano, K. Izaki, and K. Niihara, 'Microstucture and thermal conductivity of $Si_3N_4$/SiC nanocomposites fabricated from amorphous Si–C–N precursor powders', *Nanostructured Materials* 5, 809–818 (1995).

Z. Peng, X. Li, M. Zhao, H. Cai, S. Zhao, G. Hu, and B. Xu, 'Fabrication of $La_{1-x}Sr_xFe_{1-y}Co_yO_3$ sensitive ceramics, nanocrystalline thin films and the manufacture of NCTF–OSFET gas sensing device', *Thin Solid Films* 286, 270–273 (1996).

C.R. Aita and W.S. Tait, 'Nanocrystalline aluminum nitride: growth by sputter deposition, optical absorption, and corrosion protection behavior', *Nanostructured Materials* 1, 269–282 (1992).

W. S. Tait and C.R. Aita, 'Modeling corrosion behavior of aluminum– and aluminum nitride–coated steel in oxygen–free aqueous potassium chloride', *Corrosion* 46, 115–117 (1990).

W.S. Tait and C.R. Aita, 'Aluminum nitride as a corrosion protection coating for steel: the self–sealing porous electrode model', *Surface Engineering* 7, 327–330 (1991).

C.M. Scanlan, M. Gajdardziska–Josifovska, and C.R. Aita, 'Tetragonal zirconia growth by nanolaminate formation', *Applied Physics Letters* 64, 3458–3550 (1994).

C.R. Aita, M.D. Wiggins, R. Whig, C.M. Scanlon, and M. Gajdardziska–Josifovska, 'Thermodynamics of tetragonal zirconia formation in an nanolaminate film', *Journal of Applied Physics* 79, 1176–1178 (1996).

M. Schofield, C.R. Aita, P.M. Rice, and M. Gajdardziska–Josifovska, 'Transmission electron microscopy study of zirconia–alumina nanolaminates grown by reactive sputter deposition I: Zirconia nanocrystallite growth morphology', *Thin Solid Films* 326, 106–116 (1998).

C.R. Aita, 'Reactive sputter deposition of ceramic oxide nanolaminates: Zirconia–alumina and zirconia–yttria model systems', *Surface Engineering* 14, 421–426 (1998).

M. Gajdardziska–Josifovska, and C.R. Aita, 'The transformation structure of zirconia–alumina nanolaminates studied by high resolution electron microscopy', *Journal of Applied Physics* 79, 1315–1319 (1996).

M. Schofield, C.R. Ajta, P.M. Rice, and M. Gajdardziska–Josifovska, 'Transmission electron microscopy study of zirconia–alumina nanolaminates grown by reactive sputter deposition. Part I: zirconia nanocrystallite growth morphology', *Thin Solid Films* 326, 117–125 (1998).

R. Ruth, R., K. S. Mazdiyasni, P.G. Valentine, and H.O. Bielstein, 'Phase relations In the System $ZrO_2$–$Y_2O_3$ at low $Y_2O_3$ contents', *Journal of the American Ceramic Society* 67, C190–C192 (1984).

M.H. Tuilier, J. Dexpert–Ghys, H. Dexpert, and P. Lagarde, 'X–Ray absorption study of the $ZrO_2$–$Y_2O_3$ system', *Journal of Solid–State Chemistry* 69, C153–C161 (1987).

C. Pascaul and P. Duran, 'Subsolidus Phase Equilibria and Ordering in the System $ZrO_2$–$Y_2O_3$ ', *Journal of the American Ceramic Society* 66, 23–27 (1982).

H.G. Scott, 'Phase relationships in the yttria–rich part of the yttria–zirconia system', *Journal of Materials Science* 12, 311–316 (1977).

H.G Scott, 'The yttria–zirconia δ phase', *Acta Crystallographica* B33, 281–282 (1977).

R.W. Lynch and B. Morosin, 'Thermal expansion, compressibility, and polymorphism in hafium and zirconium titanates', *Journal of the American Ceramics Soceity* 55, 409–413 (1972).

A. E. McHale and R.S. Roth, 'Low–temperature phase relationships in the system $ZrO_2$–$TiO_2$', *Journal of the American Ceramics Society* 69, 827–832 (1986).

J.D. DeLoach and C.R. Aita, 'Phase evolution in sputter deposited zirconia–titania nanlaminate films', *Journal of Vacuum Science and Technology A,* in review (1999).

J.D. DeLoach and C.R. Aita, 'High refractive index <100> textured cubic zirconia formed in nanolaminates using titania interruption layers', *Journal of Materials Science Letters,* in review (1999).

W. Ensinger, 'The influence of ion irradiation during film growth on the chemical stability of film/substrate systems', *Surface and Coatings Technology* 80, 35–48 (1996).

P.J. Martin, R.P. Netterfield, W.G. Sainty, and C.G. Pacey, 'The preparation and characterization of optical thin films produced by ion–assisted deposition', *Journal of Vacuum Science and Technology A* 2, 341–345 (1984).

L. van Leaven, M.N. Alias, and R. Brown, 'Corrosion behavior of ion plated and implanted films', *Surface and Coatings Technology* 53, 25–34 (1992).

R. Hübler, A. Schroer, W. Ensinger, G.K. Wolf, W.H. Schreiner, and I.J.R. Baumvol, 'Plasma and ion–beam–assisted deposition of multilayers for tribological and corrosion protection', *Surface and Coatings Technology* 60, 561–565 (1993).

H. Kupfer, F. Richter, S. Friedrich, and H.J. Spies, 'Deposition and properties of Ti/N carbon multilayers for corrosion protection of steel', *Surface and Coatings Technology* 74–75, 333–338 (1995).

U. Wiklund, P. Hedenquist, S. Hogmark. B. Stridh, and M. Arbell, 'Multilayer coatings as corrosion protection of zircaloy,' *Surface and Coatings Technology* 86/87, 530–534 (1996).

M. Pourbaix, 'Electromechanical corrosion of metallic biomaterials', *Biomaterials* 5, 122–134, 1984.

A. Giaimo, M.N. Alias, and R. Brown, in 'Metallic nitrides for corrosion protection in marine environments: Theory compared to experimental results', *in Proceedings of Corrosion/97* (NACE International, Houston, TX, 1997) 418/1–418/12.

L.L. Hench and E.C. Ethridge, *Biomaterials: An Interfacial Approach* (Academic, New York, NTY 1992), Ch. 5.

W.S. Tait, C.O. Huber, B.C. Begnoche, J.R. Siettmann, and C.R. Aita, 'Al, Al–N alloy, and AIN–coated steel corrosion behavior in $O_2$–free KCI solutions', *Journal of Vacuum Science and Technology A* 6, 924–927 (1988).

O. Kubaschewski and C.B. Alcock, Metallurgical Thermochemistry, (Pergamon, Oxford, UK, 1979) p. 268.

C.R. Aita, 'Tailored ceramic film growth at low temperature by reactive sputter deposition', *Critical Reviews in Solid State and Materials Sciences* 23, 205–274 (1998).

* cited by examiner

SELF-REPAIRING CERAMIC COATINGS

FIELD OF INVENTION

The present invention relates to coatings for devices and implements and the like suitable for intracorporeal applications, particularly coatings for intravascular applications.

BACKGROUND OF THE INVENTION

Biomaterials are synthetic materials used to replace or augment a part of a living system or to function in contact with living tissue. Among the many causes for mortality among human beings, cardiovascular diseases account for a major portion of such deaths. Therefore, continuous improvements in the development of new and improved biomaterials capable of replacing parts of the cardiovascular system is extremely important. The primary requirements for biomaterials for long-term implants, e.g. heart valve prostheses, stents, and vascular grafts, are biocompatibility, thrombresistivity, nontoxicity, and durability. Furthermore, biomaterials should be nonirritating to tissue and nondegradable in the harsh physiological environment, neither absorbing blood constituents nor releasing foreign substance into the bloodstream.

A key problem in interfacing a biomaterial with blood revolves around the characteristics of the implant surface. Thrombus and embolism formation at the blood-implant interface is of foremost concern, and is the technology limiting factor in implant design and materials selection.

Metal implants have been used as implants due to their toughness, i.e., the ability to absorb energy before fracture. The metals and metallic alloys commonly used for implants form passivating oxide surface layers at their interface with air. However, the passivation may become destabilized by the acidic (e.g., pH of about 5), saline nature of blood. The surface reactivity of the metallic implants at the blood-implant interface leads to bulk electrochemical corrosion and localized stress corrosion, which in turn, leads to mechanical failure of the implant and ion contamination of the blood.

Polymer implants or polymer-coated metal implants are commonly used for cardiovascular applications because of their good initial biocompatibility. However, the use of polymers poses a major problem, namely, chemical degradation over time resulting in thrombus and embolism formation as well as the production of harmful wear-related debris.

Ceramic implants offer a compromise by providing chemical inertness, hardness, and wear-resistance. However, ceramic implants exhibit the same major drawback as that for all traditional bulk ceramic structures in their inability to deform plastically under either or both static and cyclic loading. The lack of flexibility of the bulk ceramics leads to difficulty in manufacturing implants and microcracking during the implant's lifetime in the body due to fatigue failure.

SUMMARY OF THE INVENTION

The present invention is directed to a multilayered protective coating formed of ceramic materials. The coating comprising an inner component or module which has at least one, preferably two layers of ceramic materials such as zirconia, titania and alumina therein. The coating further comprises an outer component or module disposed on the inner component formed of a water swellable ceramic material capable of forming a hydrate or hydroxide compound upon contact with an oxygen containing environment, e.g. water based fluids such as blood. Preferably, ceramic material for the outer component or module comprises an aluminum, zirconium or hafnium compound, more preferably, a nitride of such materials. The presently most preferred swellable component is a hydrate or hydroxide compound such as aluminum hydroxide, aluminum hydrate, and mixtures thereof. The inner component is preferably a series of bilayers comprising zirconia and titania and zirconia and alumina. The thickness of the coating layers range from about 1 to about 100 nanometers, preferably about 1 to 50 nanometers. The overall coating thickness can range up to several microns.

Generally, the preferred nanostructure protective coating comprises a plurality of nano-scale inner ceramic layers comprising zirconia, titania, alumina, and an outer layer formed of a nitride based compound selected from the group consisting of aluminum nitride, zirconium nitride and hafnium nitride.

Furthermore, an implant comprising either or both metallic and polymeric compounds is provided having the protective coating of the present invention thereon.

DETAILED DESCRIPTION OF THE INVENTION

Figure 1:
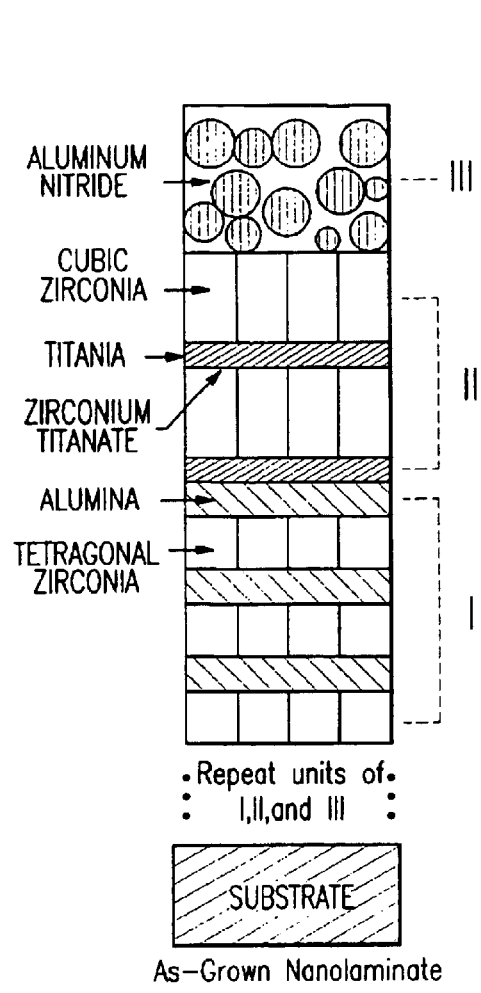
FIG. 1 is a representation of one embodiment of the nanostructure coating of the present invention.

Nanostructured materials have functional units on the order of $10^{-9}$ meter (m). In other words, the critical morphological features of nanostructures have a dimension approaching atomic distances. The morphology of nanometer-scale (nm) materials gives rise to at least two properties that either alone or in combination can produce ceramics with unique property: (1) a large internal interfacial area exhibiting unique physical and chemical behavior, and (2) the formation of unusual phases in nanocrystallites due to the finite crystal size effect, i.e., a large surface energy contribution to the total Gibbs free energy of formation when the crystallite size is small. The presence of these properties cannot be achieved in traditional ceramics having larger scale microstructures, including low-temperature ductility and superplacticity, high electrical conductivity, thermal shock resistance, enhanced gas sensing, enhanced diffusion barrier action, and enhanced corrosion resistance due to self-sealing behavior.

The protective coatings of the present invention comprise nanostructure coatings, that is coatings having a thickness in a range from about 1 to about 100 nm; preferably from about 1 nm to about 50 nm. The nanostructure coating preferably comprises a plurality of modules comprising bilayers of different ceramic materials such zirconia, alumina and titania.

A first module comprises a number (m) of zirconia ($ZrO_2$) and alumina ($Al_2O_3$) bilayers; wherein (m) is a number greater than 1. The first module provides toughness to the coating.

A second module disposed on the first module comprises a number (n) of zirconia ($ZrO_2$) and titania ($TiO_2$) bilayers;

wherein n) greater ad than 1 The second module provides hardness to the coating. Each oxide layer, that is the first and second modules, have a nanoscale lamellar structure, hence, the term nanolaminates.

A third or outer module disposed on the second module comprises a third-module compound capable of forming a hydrate or hydroxide compound upon contact in an oxygen containing environment, such as blood. The third module preferably comprises an aluminum, zirconium or hafnium compound, more preferably, a nitride of these materials. Module III comprises a single, relatively thicker layer of nanocrystalline aluminum nitride and provides corrosion resistance to the coating. Corrosion, with its electrochemical nature, is well known to be one of the quintessential issues in thrombus formation. Therefore, a coating whose outermost layer offers active corrosion protection is of utmost importance in the material design for the protective coating of the present invention. In general, the driving force for self-sealing is scaled by the decrease in Gibbs free energy that accompanies formation of the reaction product, a surface hydroxide or hydrated oxide. With respect to the ceramics used in the present nanostructure, titania, although widely used as a corrosion-resistant biomaterial because of its chemical inertness, did not self-seal and merely remained unchanged at the blood-coating interface. There was a weak driving force for zirconia and alumina to self-seal in contact with blood, i.e., a decrease in energy of 8.9 kcal/mole for zirconia and 7.8 kcal/mole for alumina. However, the conversion from aluminum nitride to aluminum hydroxide resulted in the much larger energy savings of 370 kcal/mole.

Thus, the coatings of the present invention include one or more layers of nanometer dimensions of zirconia ($ZrO_2$), titania ($TiO_2$), alumina ($Al_2O_3$), and a nitride such as aluminum nitride (AlN), zirconia nitride and hafnia nitride.

Without limiting the scope of the invention, the following one or more explanations are provided for the mechanism through which the nanostructure coatings of the present invention provide the enhanced performance.

Thermodynamic phase evolution of bulk zirconia as it is cooled from the liquid (about 2680° C. at atmospheric pressure) is as follows: cubic (about 2360° C.) to tetragonal (about 1075° C.) to monoclinic (STP phase) Transformation-toughening depends upon retention of tetragonal zirconia at room temperature and local transformation to monoclinic zirconia in response to stress. The defect structure established within the monoclinic and at the monoclinic/tetragonal boundary toughens the material.

Without limiting the scope of the invention, it is believed that transformation-toughening mechanism works as follows: The stress concentrator at the tip of a growing microcrack triggers a tetragonal-to-monoclinic zirconia transformation in a small region of material in the crack's path. The daughter monoclinic zirconia has a larger volume than its parent tetragonal zirconia, therefore applying a beneficial compressive stress to the crack tip. The crack tip "blunts" in response to this stress stopping the crack's progress. The cracked material has "repaired" itself by affecting a transformation of the material at its tip: it has retained its strength and produced toughness on demand.

Without limiting the scope of the invention, the following is believed to be a plausible mechanism by which the nanostructure coatings exhibit "self-sealing" behavior. When a substrate, such as steel, having a microstructure coating comprising nanometer-size crystallites (e.g., aluminum nitride) is exposed to an oxygen containing environment (e.g., water, blood), a chemical reaction occurs converting the surface of nanocrystallite to a hydroxide (e.g., aluminum hydroxide). The conversion results in the "swelling" of the crystallite boundaries. For example, aluminum hydroxide, with a lower density, occupies a larger volume than aluminum nitride. It is further believed that the hydroxide conversion layer around each crystallite behaves like an atomic level sealant, protecting the underlying structure (e.g., steel) from corrosion. This coating was not an inert or sacrificial coating, rather it changed in a self-limiting, beneficial manner after exposure to a water based electrolyte. Additionally, in a comparison of coatings, it was found that coatings with different crystallite size, nano-crystallinity was advantageous for self-sealing because of the large internal surface area on which a reaction product (e.g., aluminum hydroxide) can form. Specifically, a decrease in the average crystallite diameter from about 60 to about 10 nm resulted in an order of magnitude decrease in the corrosion rate.

The nanostructure coatings of the present invention are biocompatible material capable of maintaining their integrity over prolonged exposure, making them an ideal coating for metal or polymer implants.

FIG. 1 is a representation of the features of the present invention. In the embodiment, features of which are illustrated in FIG. 1, the nanostructure coating comprises a repeat unit of m=3 bilayers of zirconia-alumina, n=2 bilayers of zirconia-titania, and a single layer of nanocrystalline aluminum nitride. It should be noted, that a number of factors, alone or in combination, may be varied to achieve nanostructure of the present invention having the desired properties, examples of such factors include: (a) the number (m, n) of bilayers in modules I and II, (b) sequencing of all modules, and (c) the thickness of individual oxide layers within each nanolaminate, (d) the thickness of the nanocrystalline aluminum nitride single layer. Furthermore, it should be noted that although a coating may contain hundreds of layers, its functional properties are determined by the structure and interfaces between morphoglogical components within individual layers and the interfaces between layers, that is, at the nanometer level.

Figure 2:
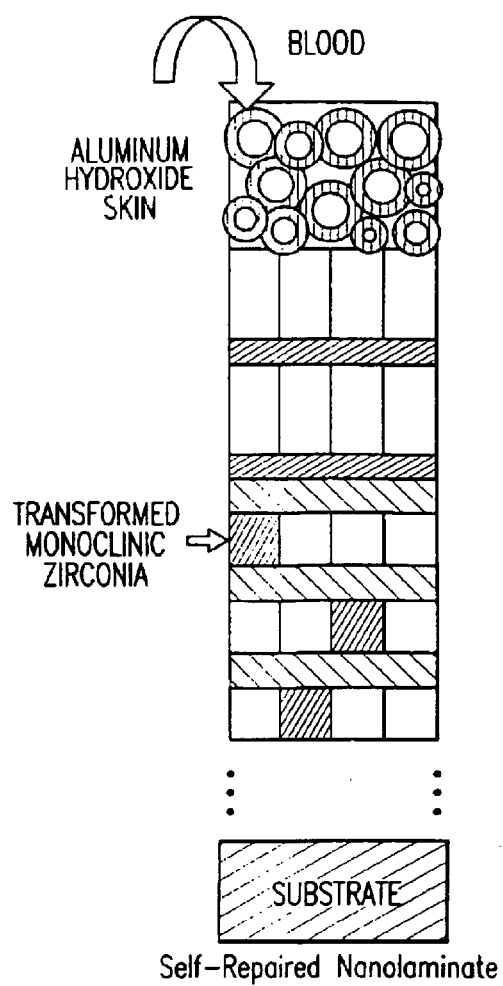
FIG. 2 is a representation of idealized changes associated with self repair in the coating shown in FIG. 1.

FIG. 2 is a representation of the idealized changes associated with self-repair. As can be seen from FIG. 2, (1) some of the tetragonal zirconia crystallites have transformed to monoclinic zirconia in response to mechanical stress in Module I; and (2) a hydroxide layer or skin has formed around the aluminum nitride nanocrystallites in Module III.

Coating Synthesis

The coatings may be grown by reactive sputter deposition in a radio frequency-excited reactor designed and built for producing ceramic multilayers. An example of such reactor is, a cryogenic pumped, 24' diameter, 304 stainless steel vacuum vessel containing three cathodes excited by three independent generators; a 20' diameter rotating anode; three quartz crystal thickness monitors; a positive feedback process gas flow system; a substrate (anode) heater; direct current substrate bias capability; and three viewing ports for optical discharge diagnostics. Preferably, the deposition system is completely programmable and automated, a desirable feature when the growth time of an individual layer in the stack is on the order of a minute. To grow the coatings, substrates are placed on the rotary table covering the anode and moved sequentially under metal targets covering the cathodes. The targets are sputtered in non-reactive gases such as $O_2$, $N_2$ in mixtures at a total pressure in the militorr range. Additionally, stainless steel and fused silica substrates are used, with the deposition proceeding at room temperature. Phase maps for sputter deposited binary oxides and nitrides may be used to guide in the selection of the process parameters.

Biocompatibility Evaluation

The biocompatibility of the coatings may be determined using in vitro optical spectrometric techniques, including infrared (IR) spectroscopy and non-linear Raman microscopy, to image the blood-coating interface. These optical techniques provide information about the local chemistry at the coatings' surface upon exposure to stationary and flowing blood, especially regarding the adsorption of blood plasma proteins, which is related to the surface's hemocompatibility. Standard tests for biocompatibility, including hemolysis and cytotoxicy tests, that measure biocompatibility in terms of changes in a volume of blood in contact with the coating, i.e., "global" tests, may also be utilized. This evaluation approach enables the association of local changes in chemistry at the blood-coating interface with commonly used benchmarks for noncompatibility obtained from standard global tests.

Optical methods are traditionally used for biomedical diagnostics where there is a need for a non-contact, non-invasive technique to study the interface between two interacting media. Traditionally, IR spectroscopy is used to determine the active vibration modes on the surface of a solid on contact with a liquid. The disadvantage of this technique is obvious when a water-based liquid is used as an interfacing medium: strong IR absorption of water reduces the useful signal and makes accurate measurements extremely difficult. The alternative spectroscopic technique is Raman scattering, which has proved to be effective for non-invasive biomedical diagnostics and blood, as well. The fundamental wavelength of the excitation radiation can be positioned in the non-absorbing region of the spectrum, e.g., at 532 nm or 1064 nm for blood, and the recorded frequency red-shifted scattered radiation contains information about vibrational modes. By confocal imaging of the interface into the detector, a high spatial resolution can be achieved.

The apparatus used for this evaluation, comprises an intracavity doubled neodimium vanadate (Nd:YVO4) laser (Millenia V. Spectra-Physics Lasers, Inc.) delivered through a focusing lens to the sample. Light scattered at 90° is collected by the 200-um diameter multimode fiber, which at the same time, serves as a confocal pinhole and delivery optics to the f/4 imaging spectrometer (TRIAX-320, Instruments Sa). The liquid nitrogen-cooled CCD camera (CCD-2000, Instruments SA, Inc.) has a 1024×256 pixel array chip. The spectrum is dispersed in the horizontal direction, and for an excitation wavelength of 532 nm, covers the range of Raman frequencies from about 110 cm–1 to 1900 cm–1. Spectral resolution is limited by the entrance fiber diameter and the dispersive grating, measured to be 15 $cm^{-1}$. A holographic notch filter (Kaiser Optical Systems, Inc.) is used to improve rejection efficiency, providing six additional orders of magnitude of laser straight light rejection up to about 110 $cm^{-1}$ from the 532-nm laser line. The total straight light rejection is estimated be higher than 10 orders of magnitude.

Figure 3:
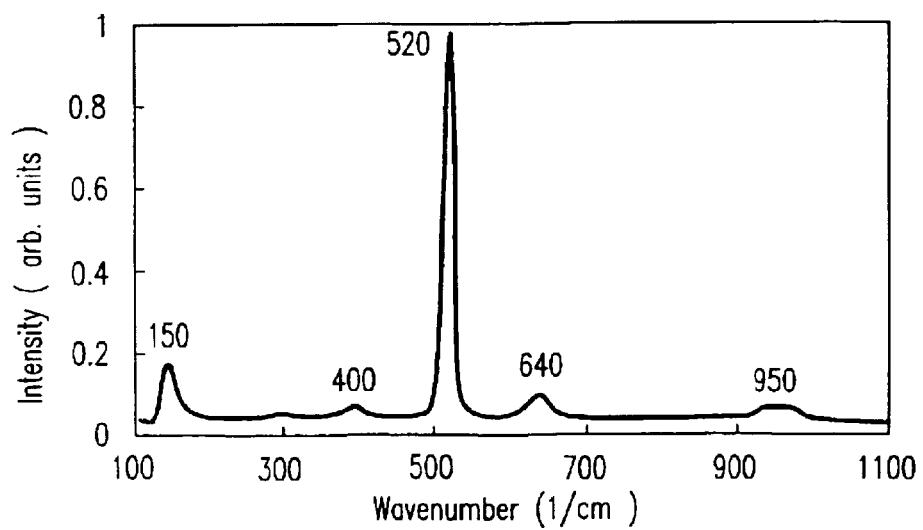
FIG. 3 is representation of a Raman spectrum of a single layer nanocrystalline titania.

A typical Raman spectrum of a single layer nanocrystalline titania is shown in FIG. 3, The film thickness was about 700 nm, and the substrate was a single crystal silicon from which the native oxide had not been removed prior to deposition. The 520 $cm^{-1}$ LO-phonon line of silicon is clearly seen in this spectrum. The 150 $cm^{-1}$ and 640 $cm^{-1}$ peaks correspond to the $E_g$ mode and 400 $cm^{-1}$ to $B_{1g}$ mode of anatase phase of titania. The relatively strong line around 950 $cm^{-1}$ is attributed to silicon-oxygen-titanium bond formation, indicating that there is a strong interaction at the interface between the titania film and the native silicon dioxide layer on the silicon substrate. This flatter feature illustrates the sensitivity of Raman spectroscopy to detection of oxide interfaces.

The same type of measurement may be made on the interface of the nanostructured ceramic coatings and blood. These experiments may be done before and after the coating is exposed to blood. Proteins from the blood that are absorbed on the ceramic coating's surface will appear in the Raman spectra. For example, Characteristic peaks corresponding to amid I (about 1640 $cm^{-1}$) and amid II (about 1540 $cm^{-1}$) bands with some modifications due to interaction with ceramic surface are expected appear. The spectroscopic studies may then be compared with the results of the standard biocompatibility tests.

To study the real-time in vitro studies, with the ceramic nano laminate in direct contact with stationary and flowing blood, Raman spectroscopy may be used. Other parallel methods may also be used to minimize the effect of possible fluorescent background from the blood, for example, Fourier Transform Raman spectroscopy and nonlinear Raman spectroscopy (Coherent anti-Stokes Raman spectroscopy—CARS). The latter technique has several advantages over traditional Raman spectroscopy, namely: (1) the CARS signal is much stronger when short (picosecond) laser pulses are used; (2) the CARS signal is blue-shifted from the two pump pulses, and thus the fluorescent background may not be a problem; and (3) the CARS signal is highly spatially localized, i.e., it originates only from the focal point of the laser beam, the position at which the laser radiation intensity.

A real-time nonlinear Raman microscope may be used comprising a tunable short pulse laser source, a titanium sapphire amplifier, and an optical parametric amplifier. The detection apparatus comprises the same spectrometer and CCD camera used for the Raman studies, but the holographic notch filter is be replaced with a short-wavelength pass filer to select the blue-shifted CARS signal. At least six orders of magnitude improvement in the signal amplitude for the same average laser power, compared to Raman, may be achieved by this technique. Thus, for the same signal-to-noise ratio, several orders of magnitude less pump power is needed, reducing the thermal load and avoiding many unwanted effected associated with heating. This approach will provide for an instrument for in vitro real-time microscopic diagnostics of biomaterials on the blood interface.

Surface Studies

Scanning electron microscopy (SEM) may be used to study the morphology of the coating surface before and after exposure to blood, including imaging of absorbates. X-ray photoelectron and Auger spectroscopies may be used for chemical specification and chemical bonding characteristics of the material and any adsorbate present before and after exposure to blood.

Electrochemical Corrosion Studies

Direct current polarization (DC) electrochemical impedance spectroscopy (EIS), and bulk electrolyte pH determination may be carried out on selected nanolaminates on steel substrates. As a reference, bare steel substrates may also be tested. Current-voltage relationships may be obtained from DC measurements under cathodic polarization. The open circuit potential and corrosion current may then be determined from a Tafel polot (cathodic polarization curve) of current-voltage data. EIS may be used to investigate changes in the electrical double layer (EDL) that develops at the sample's surface when immersed in blood. The capacitance and resistance of the EDL are derived from its chemical composition. Different mechanisms of charge transport through the EDL respond to perturbation at different frequencies. EIS is therefore especially useful for understanding the kinetic process steps associated with corrosion of a ceramic-coated implant by blood. Bulk electrolyte pH values may be determined as a function of exposure time over a period of seven days.

EXAMPLES

Example I
Transformation-Toughening Zirconia-Alumina Coatings

Nanolaminates consisting of polycrystalline zirconia and vitreous alumina bilayer stacks were grown at room temperature by reactive sputter deposition. The formation of tetragonal zirconia in the as-grown material was consistent with a finite crystallite size effect. Solely the tetragonal phase was produced in zirconia layers whose thickness was less than a critical value, e.g., less than 6 nm for room temperature growth. With respect to in-service transformation-toughening, high resolution transmission electron microscopy (HREM) was used to study the post-deposition, stress-induced tetragonal to monoclinic zirconia transformation, and its plane and direction invariants were identified.

The transformation was localized to nano-sized regions within individual zirconia layers, constrained by the alumina. The macroscopic effect of the toughness resulting from this transformation was confirmed by scanning electron microscopy of a cross-sectioned fracture surface of a nanolaminate growth on a silicon wafer. A crack originating in the silicon wafer was terminated at the wafer-nanolaminate interface, indicating that the nanolaminate had remained intact and adherent to the silicon substrate.

Example II
Cubic Zirconia and Zirconia Titanate Formation Zirconia-Titania Nanolaminates at Room Temperature As the thickness of each constituent layer in a nanolaminate decreases, the interface between layers plays an increasingly important role in determining the overall properties of the coating. In turn, chemical reactivity between constituents plays an important role in determining the properties of the interface, even at low growth temperature. To illustrate this point, two pseudobinary oxide systems that represented extremes in chemical reactivity between constituents were compared, namely, zirconia-alumina and zirconia-yttria. The pseudobinary equilibrium phase diagram of zirconia and alumina showed very limited mutual solid solubility and no compounds. On the other hand, the pseudobinary phase diagram of zirconia and yttria showed a series of solid solutions (alloys) covering the entire composition range from pure zirconia to pure yttria, as well as compounds. These two model systems allowed comparison of the effects of chemical reactivity between constituents at their interface in nanolaminates with the same nominal architecture. The results showed that in zirconia-alumina nanolaminates, each binary oxide constituent was a separate entity and their interface was incoherent. In zirconia-yttria nanolaminates, an interfacial reaction between constituents completely obliterated yttria as a separate entity. The reaction product, yttria-stabilized cubic zirconia, grew in the form of needle-like crystallites. These results demonstrated the ability to form interfacial oxide solid solutions at low temperature in a system in which the bulk equilibrium phase diagram predicts reaction between oxide components. Coatings consisting entirely of interface reaction products can therefore be fabricated if the bilayer spacing is small enough.

Thereafter, zirconia-titania nanolaminates were designed having specific phases and interfaces. The bulk zirconia-titania phase diagram showed three zirconium titanate compounds with closely-related structures: $ZrTiO_4$, $ZrTi_2O_6$, $Zr_5Ti_7O_{24}$; and two alloy phases with limited mutual solid solubility. It was also found that zirconia and titania were reactive during room temperature sputter deposition, with zirconium titanate forming at the bilayer interface. Micron-thick nanolaminates nominally consisting of ultrathin (1.5 nm) zirconia and titania layers actually consisted entirely of their reaction product. Furthermore, the interfacial stress associated with the reaction led to the stabilization of cubic zirconia in nanolaminates with thicker (about 16 to about 22 nm) zirconia layers.

Example III
Nanocrystalline Aluminum Nitride for Self-Sealing Corrosion Protection of Steel Traditionally, ceramic coatings are used to protect an underlying material from corrosion by providing an inert, non-porous barrier to diffusion. In that case, any defect in the coating, such as a microscopic pore or pinhole, is a possible source of failure due to pitting corrosion. In addition, polycrystalline coatings with a typical columnar crystal structure are intrinsically vulnerable, because this microstructure provides fast diffusion paths to the substrate. To remedy the intrinsic problem of a columnar microstructure, multilayer coatings may be used to interrupt crystallite growth. However, pitting corrosion due to microscopic defects is still a concern.

The present inventors identified another, active, type of corrosion protection by ceramic coatings, referred to here as "self-sealing" behavior. To develop the self-sealing ceramic coating aluminum nitride coating on steel, as the prototype material, was utilized. The coating microstructure comprised nanometer-size crystallites. When exposed to water, a chemical reaction converted the surface of each nanocrystallite to a hydroxide. The result was that crystallite boundaries "swelled", since aluminum hydroxide, with a lower density, occupied a larger volume than aluminum nitride. The hydroxide conversion layer around each crystallite behaved like an atomic level sealant; protecting the underlying steel from corrosion. The coating was not inert or sacrificial, but changed in a self-limiting, beneficial manner after exposure to the electrolyte. In a comparison of coatings with different crystallite size, nanocrystallinity was an advantage for self-sealing because of the large internal surface area on which a reaction product can form. Specifically, a decrease in the average crystallite diameter from about 60 to about 10 nm resulted in an order of magnitude decrease in the corrosion rate.

What is claimed is:

1. An intracorporeal device having a protective self-repairing coating on a surface thereof, comprising:
  a. an inner coating component which is on the surface of the device and which has at least one bilayer comprising a first layer formed of a first ceramic material and a second layer formed of a second ceramic material different from the first ceramic material; and
  b. an outer coating component which is on the inner coating component and which has at least one layer less than 100 nm thick formed of nano-crystalline aluminum nitride that forms a water swellable material in an oxygen containing medium.

2. The intracorporeal device of claim 1 wherein the first and second ceramic materials are selected from the group consisting of zirconia, titania and alumina.

3. The intracorporeal device of claim 1 wherein the water swellable material is aluminum hydrate or aluminum hydroxide.

4. The intracorporeal device of claim 1 wherein individual bilayers of the inner coating component are about one to about 100 nanometers thick.

5. The intracorporeal device of claim 1 wherein the individual bilayers of the inner coating are about one to about 50 nanometers thick.

6. The intracorporeal device of claim 1 wherein the Inner coating component has at least one bilayer with zirconia in one layer and alumina in the other layer.

7. The intracorporeal device of claim 1 wherein the inner coating component has at least one bilayer with zirconia in one layer and titania in the other.

8. The intracorporeal device of claim 1 wherein the inner component has a thickness of up to about a micron.

9. The intracorporeal device of claim 1 wherein each of the inner and outer coating components have a thickness in a range from about 1 to 50 nm.

10. The intracorporeal device of claim 1 wherein the at least one bilayer on the surface of the device includes a nanoscale hardness-imparting ceramic coating layer and a nano-scale toughness-imparting ceramic coating layer.

11. The intracorporeal device of claim 1 wherein each of the harness-imparting and the toughness-impairing coating layer has a thickness independently ranging from about 1 to about 100 nm.

12. The intracorporeal device of claim 1 wherein the outer coating component has a thickness in the range from about 1 to less than 100 nm.

13. A nanostructure protective self-repairing coating for a substrate, comprising:
   a. an outer coating component which is less than 100 nm thick, which is formed of a nanocrystalline compound selected from the group consisting of aluminum nitride, zirconium nitride and hafnium nitride capable of forming a hydrate or hydroxide compound upon contact with an oxygen containing environment and
   b. an inner coating component secured to the substrate which is formed of at least one bilayer which has a first layer of a first ceramic material and a second layer of a second ceramic material that is different from the first ceramic material.

14. The coating of claim 13 wherein the compound of the outer coating component comprises aluminum nitride.

15. An intracorporeal implant, comprising:
   a substrate selected from the group consisting of metals, polymers, and a combination thereof; and
   a protective coating thereon having a plurality of coating components comprising:
   a first coating component having at least one bilayer wherein each layer is formed of a material selected from the group consisting of zirconia and alumina;
   a second coating component disposed on the first coating component having at least one bilayer with each layer formed of a material selected from the group consisting of zirconia and titania; and
   a third coating component disposed on the second coating component formed of a compound which has microcrystallinity and which is capable of forming a hydrate or hydroxide upon contact with an oxygen containing environment.

16. The implant of claim 15 wherein the compound is an aluminum compound.

17. The implant of claim 15 wherein the compound is an aluminum nitride.

18. The implant of claim 15 wherein the compound selected is aluminum nitride which forms aluminum hydroxide, aluminum hydrate, or mixtures thereof.

19. The implant of claim 15 wherein the coating thickness is in a range from about 1 to about 100 nanometers.

20. The implant of claim 15 wherein the coating thickness is in a range from about 1 to 50 nanometers.

21. An intracorporeal implant which has a substrate selected form the group consisting of metals, polymers, and a combination thereof,
   a. which has an inner coating component secured to the substrate with at least one bilayer formed of a first layer of a first ceramic material and a second layer of a second ceramic material different from the first ceramic material and
   b. which has a protective, self-repairing outer coating component having a thickness of less than 100 nm, having nano-crystallinity and comprising a ceramic material forted of a compound selected from the group consisting of aluminum nitride, zirconium nitride and hafnium nitride and capable of forming a hydrate or hydroxide compound upon contact with an oxygen containing environment.

22. The implant of claim 21 wherein the compound is aluminum nitride.

23. The implant of claim 21 wherein the coating further includes a plurality of nanoscale ceramic bilayers including a hardness-imparting bilayer and a toughness-impairing bilayer.

* * * * *

UNITED STATES PATENT AND TRADEMARK OFFICE
CERTIFICATE OF CORRECTION

PATENT NO. : 6,869,701 B1
DATED : March 22, 2005
INVENTOR(S) : Aita et al.

It is certified that error appears in the above-identified patent and that said Letters Patent is hereby corrected as shown below:

Column 9,
Line 7, change "Inner" to -- inner --

Column 10,
Line 35, change "forted" to -- formed --.
Line 43, change "nanoscale" to -- nano-scale --.

Signed and Sealed this

Thirty-first Day of May, 2005

JON W. DUDAS
*Director of the United States Patent and Trademark Office*